United States Patent
She et al.

(10) Patent No.: US 11,702,582 B2
(45) Date of Patent: Jul. 18, 2023

(54) BIOCHEMICAL VISCOSITY REDUCER FOR HEAVY OIL AND PREPARATION METHOD THEREOF

(71) Applicant: Yangtze University, Wuhan (CN)

(72) Inventors: Yuehui She, Wuhan (CN); Fan Zhang, Wuhan (CN); Zhi Zhang, Wuhan (CN); Puyong Yao, Wuhan (CN); Fei Li, Wuhan (CN); Hao Dong, Wuhan (CN); Shanshan Sun, Wuhan (CN); Gaoming Yu, Wuhan (CN); Shaojin Yi, Wuhan (CN); Wenda Zhang, Wuhan (CN); Linqi Hu, Wuhan (CN); Yangyang Feng, Wuhan (CN); Anying Zheng, Wuhan (CN); Yang Li, Wuhan (CN)

(73) Assignee: Yangtze University, Wuhan (CN)

( * ) Notice: Subject to any disclaimer, the term of this patent is extended or adjusted under 35 U.S.C. 154(b) by 183 days.

(21) Appl. No.: 17/226,426

(22) Filed: Apr. 9, 2021

(65) Prior Publication Data

US 2022/0041919 A1 Feb. 10, 2022

(30) Foreign Application Priority Data

Aug. 7, 2020 (CN) .......................... 202010790705.3

(51) Int. Cl.
| | | |
|---|---|---|
| *C09K 8/582* | (2006.01) | |
| *C09K 8/584* | (2006.01) | |
| *C12N 1/20* | (2006.01) | |

(52) U.S. Cl.
CPC .............. *C09K 8/582* (2013.01); *C09K 8/584* (2013.01); *C12N 1/20* (2013.01)

(58) Field of Classification Search
CPC .......... C09K 8/582; C09K 8/584; C09K 8/54; C12N 1/20; C12N 9/00; C12R 2001/01
See application file for complete search history.

(56) References Cited

U.S. PATENT DOCUMENTS 9,598,944 B2    3/2017 Frank
2021/0301191 A1*  9/2021 Farmer ................... E21B 43/16

FOREIGN PATENT DOCUMENTS

| CN | 101407777 A | * | 4/2009 |
| CN | 108130064 A | * | 6/2018 |
| CN | 108130064 A | | 6/2018 |
| CN | 108148565 A | | 6/2018 |
| CN | 109852361 A | * | 6/2019 |

* cited by examiner

*Primary Examiner* — Kumar R Bhushan
(74) *Attorney, Agent, or Firm* — The Dobrusin Law Firm, P.C.

(57) ABSTRACT

A biochemical viscosity reducer for heavy oil and a preparation method thereof. The viscosity reducer includes: *Brevibacillus borstelensis*-fermented mixed lipopeptide solution: 30 to 60 parts; compound biological enzyme: 15 to 30 parts; plant-based nonionic surfactant: 10 to 20 parts; antibacterial agent: 1 to 5 parts; stabilizer: 1 to 5 parts; and alcohol solvent: 10 to 20 parts; where, the above components are measured by mass. The preparation method includes: step 1: adding 30 to 60 parts of a *Brevibacillus borstelensis*-fermented mixed lipopeptide solution, 15 to 30 parts of a compound biological enzyme, 10 to 20 parts of a plant-based nonionic surfactant, and 1 to 5 parts of a stabilizer to a reactor; and step 2: adding 1 to 5 parts of an antibacterial agent and an alcohol solvent to the reactor, and stirring a resulting mixture for 60 min to 120 min.

8 Claims, No Drawings

BIOCHEMICAL VISCOSITY REDUCER FOR HEAVY OIL AND PREPARATION METHOD THEREOF

TECHNICAL FIELD

The present disclosure relates to the technical field of additives for petroleum exploitation, and in particular to a biochemical viscosity reducer for heavy oil and a preparation method thereof.

BACKGROUND

As an unconventional crude oil resource, heavy oil accounts for more than 30% of the global proven crude oil reserves. The output of light crude oil that is easy to be exploited is declining, but the demand for petroleum resources is increasing year by year. Therefore, it is more urgent to exploit heavy oil. Heavy oil is a relatively viscous crude oil, which is difficult to be extracted and transported mainly due to high colloidal asphaltene content and poor fluidity. In addition, asphaltenes are inevitably precipitated during an exploitation process in heavy oil reservoirs, which will block seepage channels for an oil layer, thereby affecting output and even leading to production shutdown. Adding chemical viscosity reducers or light crude oil is a conventional method for heavy oil exploitation. However, the method of adding chemical viscosity reducers has the following disadvantages: difficult emulsification in heavy oil formations at an early stage, difficult demulsification and dehydration at a late stage, high cost, non-environmental friendliness, and so on. The method of adding light crude oil requires large light crude oil consumption and high cost, and cannot achieve exploitation in reservoirs without light crude oil sources. Therefore, it is necessary to develop environmentally-friendly viscosity reducers for heavy oil.

Biosurfactant (BS) refers to surfactants with an amphiphilic structure produced from microbial metabolism. BS can disperse and emulsify crude oil and greatly reduce the viscosity of crude oil, which is an important mechanism for microbial enhanced oil recovery (MEOR). BS mainly includes glycolipids produced by *Pseudomonas* and lipopeptides produced by *Bacillus*, both of which can significantly reduce an oil-water interfacial tension, peel off crude oil from a rock pore surface, and disperse and emulsify the crude oil. *Bacillus* is a genus of indigenous microorganisms with an oil recovery function that are widely present in oil reservoirs.

For example, U.S. Pat. No. 9,598,944 (Enzyme enhanced oil recovery) discloses that biological enzymes have been used to improve oil recovery efficiency. Biological enzymes are proteins with specificity that serve as high efficiency catalysts at mild reaction conditions. According to reports, biological enzymes show a catalytic efficiency 106 to 1,014 times higher than general chemical catalysts. Biological enzymes are environmentally-friendly, surface-active substances produced by microorganisms, which usually work at a very low concentration. Moreover, it has been found that the addition of a modified biological enzyme solution in laboratory core flooding and field tests will increase an oil production. Biological enzymes achieve oil recovery mainly based on the following mechanisms: (1) A protein film is formed on the surface of a rock to change the wettability of the rock so that the rock is more hydrophilic. The biological enzymes make a rock surface hydrophilic through hydrogen bonding with water molecules. (2) The viscosity or interfacial tension of oil is reduced through emulsification. Biological enzymes composed of hydrophilic and lipophilic molecules have an amphiphilic structure, and can be micellized at an interface to reduce an interfacial tension. Wettability is an important factor that controls the location, flow, and distribution of fluids in a reservoir. The impact of wettability on oil recovery has been discussed in some documents. Many researchers have tried to advantageously change the wettability in a reservoir to improve the spontaneous absorption of water and water flooding performance, thereby enhancing oil recovery. Enzymes are a set of specific proteins synthesized by viable cells, which can serve as catalysts for thousands of biochemical reactions. Enzymes can be used to produce desired chemicals and can also be used to degrade undesired chemicals. Enzymes catalyze chemical reactions based on the following mechanism: when a substrate reaches an active site of an enzyme, the active site will reduce activation energy required by the reaction to accelerate or catalyze the reaction; the substrate is then converted into a product; finally, the enzyme is released from the active site and then used as a catalyst for the next reaction; and the enzyme is recycled as above.

Enzymes include hydrolases, transferases, lyases, isomerases, ligases, oxidoreductases, etc. Different enzymes have different functions. Most enzymes currently used in industry are hydrolases of many different types. For example, protease (hydrolyzing peptides), amidase (hydrolyzing amides), halidase (hydrolyzing halides), esterase (hydrolyzing esters), and lipase (hydrolyzing triglyceride (TG)) break down some compounds through hydrolysis. In recent years, many researchers have conducted research and reports on use of enzymes in the petroleum industry.

Fungi and enzymes produced by fungi can decompose heavy components in heavy oil such as polycyclic aromatic hydrocarbons (PAHs) and colloidal asphaltenes, which has become a new highlight in MEOR. It is reported that some microorganisms such as fungi can oxidize asphaltenes because they have special enzymes such as peroxidase and laccase; and some hemeproteins such as chloroperoxidase (CPO), cytochrome c peroxidase (CCP), cytochrome c reductase (CCR), and lignin peroxidase (LiP), and LiP from *Bacillus megaterium* and *Escherichia coli* can achieve biocatalytic reforming of asphaltenes to remove nickel and vanadium in petroleum porphyrins and asphaltenes. Recently, it has been reported that *Daedaleopsis* sp. isolated from wood-degrading fungi has the effect of degrading asphaltenes and dibenzofurans. The microorganism, after cultivated for 14 d at 40° C. and pH 5, can consume more asphaltenes and can biologically degrade 88.7% of asphaltenes in crude oil. Definite experimental evidence of enzymes capable of modifying asphaltene molecules has been reported. CPO in *Aspergillus fumigatus* can convert petroleum porphyrins and asphaltenes, which shows a significantly-improved modification effect on porphyrins in a system with organic solvents and a water system. The cation of cytochrome C from horse heart can highly act upon asphaltenes and petroleum porphyrins. Polyethylene glycol (PEG) can be used to chemically modify a protein surface to obtain a protein-polymer conjugate that is soluble in organic solvents. In addition, methyl esterification of heme propionate can increase the hydrophobicity of active sites. Fungal enzymes degrade asphaltenes in heavy oil and remove heavy metals such as nickel and vanadium therein, thus effectively reducing the viscosity of heavy oil, peeling off crude oil, and improving the fluidity of heavy oil.

As another example, Chinese patent CN108130064 discloses a *Bacillus subtilis* BS viscosity reducer for heavy oil, but in the patent, an anionic surfactant of alkyl sulfonate and an nonionic surfactant of alkyl alcohol amine polyether are added, which cannot be completely degraded by microorganisms, increasing the difficulty in dehydration at a late stage and the stress on environmental protection.

As another example, Chinese patent CN108148565A discloses an ionic liquid (IL) viscosity reducer for heavy oil and a method for preparing the same using BS. In the present disclosure, a microbial lipopeptide is introduced into an anionic or cationic IL based on the above-mentioned patent (CN108130064), which increases costs and environmental risks.

At present, there are no detailed reports on the preparation of viscosity reducers for heavy oil by combining a BS with a biological enzyme.

SUMMARY

Based on the aforementioned technical gaps in the prior art, the present disclosure provides a biochemical viscosity reducer for heavy oil and a preparation method thereof.

The biochemical viscosity reducer for heavy oil of the present disclosure includes:

*Brevibacillus borstelensis*-fermented mixed lipopeptide solution: 30 to 60 parts;
compound biological enzyme: 15 to 30 parts;
plant-based nonionic surfactant: 10 to 20 parts;
antibacterial agent: 1 to 5 parts;
stabilizer: 1 to 5 parts;
alcohol solvent: 10 to 20 parts; and
where, the above components are measured by mass.

Further, the compound biological enzyme may refer to a combination of any four or more of esterase, lipase, protease, amylase, cellulase, amidase, oxidoreductase, fungal laccase, and peroxidase.

Further, the plant-based nonionic surfactant may be tea saponin.

Further, the stabilizer may include disodium ethylenediaminetetraacetic acid (EDTA) and/or sodium citrate.

Further, the antibacterial agent may include tetrakis(hydroxymethyl)phosphonium sulfate (THPS) and/or potassium benzoate.

Further, the alcohol solvent may include one or more of ethylene glycol (EG), propylene glycol (PG), and butylene glycol.

The present disclosure also provides a preparation method of a biochemical viscosity reducer for heavy oil, including the following steps:

step 1: adding 30 to 60 parts of a *Brevibacillus borstelensis*-fermented mixed lipopeptide solution, 15 to 30 parts of a compound biological enzyme, 10 to 20 parts of a plant-based nonionic surfactant, and 1 to 5 parts of a stabilizer to a reactor, and stirring a resulting mixture at a controlled temperature of 50° C. to 60° C. for 50 min to 80 min; and step 2: adding 1 to 5 parts of an antibacterial agent and an alcohol solvent to the reactor, and stirring a resulting mixture for 60 min to 120 min, cooling to room temperature, and standing for 2 h to obtain a finished product of the viscosity reducer.

Further, the plant-based nonionic surfactant may be tea saponin; the antibacterial agent may include THPS and potassium benzoate; and the stabilizer may include disodium EDTA and sodium citrate.

Compared with the prior art, the present disclosure has the following advantages:

1. The biochemical viscosity reducer for heavy oil in the present disclosure adopts the *Brevibacillus borstelensis*-fermented mixed lipopeptide solution as a microbial metabolite lipopeptide BS, which has the functions of wetting, emulsifying, and dispersing, and can dissolve, solubilize, and destroy asphaltene aggregates in heavy oil.

2. The biochemical viscosity reducer for heavy oil in the present disclosure adopts four or more of esterase, lipase, protease, amylase, cellulase, amidase, oxidoreductase, fungal laccase, and peroxidase as a compound biological enzyme, which can quickly peel off heavy oil from the surface of rocks and minerals, destroy fused-ring aromatic structures formed by porphyrins and heavy metals in heavy oil, and reduce complexing forces of fused-ring aromatic hydrocarbons with rocks and minerals.

3. The biochemical viscosity reducer for heavy oil in the present disclosure adopts tea saponin as a nonionic surfactant, which, in combination with the BS, quickly disperses the emulsifies heavy oil.

4. The biochemical viscosity reducer for heavy oil in the present disclosure adopts disodium EDTA and sodium citrate as a stabilizer, which can effectively eliminate the inactivation effect of high-valence ions in a reservoir environment on an anionic lipopeptide BS and thus eliminate organic precipitates.

5. The biochemical viscosity reducer for heavy oil in the present disclosure adopts THPS and potassium benzoate as an antibacterial agent, which can maintain the long-term stability of the viscosity reducer, inhibit harmful microorganisms such as SRB, and can be completely degraded by microorganisms, thus resulting in no environmental hazards.

Description of Deposit

Deposit address: Institute of Microbiology, Chinese Academy of Sciences, No. 3, Courtyard 1, Beichen West Road, Chaoyang District, Beijing, China;

deposit date: Nov. 18, 2014;
strain name: *Brevibacillus borstelensis*;
deposit institute: China General Microbiological Culture Collection Center;
abbreviation of deposit institute: CGMCC; and
deposit number: CGMCC No. 9981.

DETAILED DESCRIPTION

In order to illustrate the above objectives, features and advantages of the present disclosure more clearly, the present disclosure will be further described in detail below in conjunction with specific implementations. It should be noted that the examples in the application and features in the examples may be combined with each other in a non-conflicting situation.

Example 1

The biochemical viscosity reducer for heavy oil included 50 parts of a *Brevibacillus borstelensis*-fermented mixed lipopeptide solution (a crude lipopeptide solution, available lipopeptide content: 3 parts), 18 parts of a compound biological enzyme (including 5 parts of protease, 5 parts of esterase, 5 parts of oxidoreductase, and 3 parts of laccase), 12 parts of a plant-based nonionic surfactant (tea saponin), 2 parts of an antibacterial agent (THPS), 3 parts of a stabilizer (disodium EDTA), and 15 parts of a solvent (a mixture of PG and butylene glycol (1:1)), where, the above components were measured by mass. The *Brevibacillus borstelensis*-fermented mixed lipopeptide solution, compound biological enzyme, tea saponin, and disodium EDTA were added to a 2,000 L ceramic reactor according to the above-mentioned ratio, and a resulting mixture was thoroughly stirred, heated to 55° C., and kept at the temperature for 60 min; and then the antibacterial agent and alcohol solution were added according to the above-mentioned ratio, and a resulting mixture was stirred and incubated for 60 min, cooled to room temperature, and discharged to obtain a finished product 1 of the viscosity reducer for heavy oil. The *Brevibacillus borstelensis* conducted fermentation in LB medium at a pH of 5 to 9.5 and a temperature of 20° C. to 60° C.

Example 2

The biochemical viscosity reducer for heavy oil included 40 parts of a *Brevibacillus borstelensis*-fermented mixed lipopeptide solution (a crude lipopeptide solution, available lipopeptide content: 4 parts), 22 parts of a compound biological enzyme (including 4 parts of amylase, 4 parts of protease, 5 parts of esterase, 5 parts of oxidoreductase, and 4 parts of laccase), 15 parts of a plant-based nonionic surfactant (tea saponin), 3 parts of an antibacterial agent (THPS), stabilizer (2 parts of sodium citrate and 2 parts of disodium EDTA), and 16 parts of a solvent (a mixture of EG, PG, and butylene glycol (1:1:1)), where, the above components were measured by mass. The *Brevibacillus borstelensis*-fermented mixed lipopeptide solution, compound biological enzyme, tea saponin, sodium citrate, and disodium EDTA were added to a 2,000 L ceramic reactor according to the above-mentioned ratio, and a resulting mixture was thoroughly stirred, heated to 58° C., and kept at the temperature for 70 min; and then the antibacterial agent and alcohol solution were added according to the above-mentioned ratio, and a resulting mixture was stirred and incubated for 80 min, cooled to room temperature, and discharged to obtain a finished product 2 of the viscosity reducer for heavy oil.

Example 3

The biochemical viscosity reducer for heavy oil included 52 parts of a *Brevibacillus borstelensis*-fermented mixed lipopeptide solution (a crude lipopeptide solution, available lipopeptide content: 3 parts), 20 parts of a compound biological enzyme (including 3 parts of amidase, 4 parts of protease, 5 parts of esterase, 3 parts of cellulase, 3 parts of oxidoreductase, and 2 parts of laccase), 11 parts of a plant-based nonionic surfactant (tea saponin), an antibacterial agent (2 parts of THPS and 2 parts of potassium benzoate), 3 parts of a stabilizer (disodium EDTA), and 10 parts of a solvent (a mixture of EG and butylene glycol (1:1)), where, the above components were measured by mass. The *Brevibacillus borstelensis*-fermented mixed lipopeptide solution, compound biological enzyme, tea saponin, and disodium EDTA were added to a 2,000 L ceramic reactor according to the above-mentioned ratio, and a resulting mixture was thoroughly stirred, heated to 53° C., and kept at the temperature for 80 min; and then the antibacterial agent and alcohol solution were added according to the above-mentioned ratio, and a resulting mixture was stirred and incubated for 90 min, cooled to room temperature, and discharged to obtain a finished product 3 of the viscosity reducer for heavy oil.

Example 4

The biochemical viscosity reducer for heavy oil included 45 parts of a *Brevibacillus borstelensis*-fermented mixed lipopeptide solution (a crude lipopeptide solution, available lipopeptide content: 4 parts), 20 parts of a compound biological enzyme (including 3 parts of amylase, 5 parts of protease, 4 parts of esterase, 6 parts of oxidoreductase, and 2 parts of laccase), 16 parts of a plant-based nonionic surfactant (tea saponin), 4 parts of an antibacterial agent (THPS), stabilizer (2 parts of sodium citrate and 3 parts of disodium EDTA), and 10 parts of a solvent (a mixture of butylene glycol and PG (1:1)), where, the above components were measured by mass. The *Brevibacillus borstelensis*-fermented mixed lipopeptide solution, compound biological enzyme, tea saponin, sodium citrate, and disodium EDTA were added to a 2,000 L ceramic reactor according to the above-mentioned ratio, and a resulting mixture was thoroughly stirred, heated to 55° C., and kept at the temperature for 80 min; and then the antibacterial agent and alcohol solution were added according to the above-mentioned ratio, and a resulting mixture was stirred and incubated for 90 min, cooled to room temperature, and discharged to obtain a finished product 4 of the viscosity reducer for heavy oil.

The viscosity-reducing effects of the viscosity reducers for heavy oil prepared in the above Examples 1 to 4 on super heavy oil in a specified oil field are shown in Table 1 below:

TABLE 1

Viscosity-reducing effects of Examples 1 to 4 on super heavy oil

| No. | Example 1 | Example 2 | Example 3 | Example 4 |
|---|---|---|---|---|
| Viscosity of dehydrated crude oil (mPa · s) | 20574 | 19431 | 19812 | 20955 |
| Viscosity-reducing rate for dehydrated crude oil (%) | 46 | 49 | 48 | 45 |
| Viscosity of emulsified crude oil (mPa · s) | 103 | 66 | 96 | 107 |
| Viscosity-reducing rate for emulsified crude oil (%) | 99.73 | 99.83 | 99.75 | 99.72 |

Notes: mineralization: 150,000 ppm, original heavy oil viscosity: 38,100 mPa · s, temperature: 60° C., speed: 200 rpm, and torque: 70.

The viscosity reducer for heavy oil prepared in the present disclosure adopts a microbial metabolite and a biological enzyme as main components, uses additive components that can be degraded by microorganisms, and can achieve a viscosity-reducing rate of more than 40% for dehydrated heavy oil. The viscosity reducer can emulsify heavy oil into oil-in-water emulsion, which leads to a viscosity-reducing rate of more than 99%. Therefore, the present disclosure shows promising application prospects in the recovery under viscosity reduction and the transportation of heavy oil.

The present disclosure is not limited by the aforementioned examples. The aforementioned examples and the description only illustrate the principle of the present disclosure. Various changes and modifications may be made to the present disclosure without departing from the spirit and scope of the present disclosure. Such changes and modifications all fall within the claimed scope of the present disclosure. The protection scope of the present disclosure is defined by the appended claims.

What is claimed is:

1. A biochemical viscosity reducer for heavy oil, comprising:
   *Brevibacillus borstelensis*-fermented mixed lipopeptide solution: 30 to 60 parts;
   compound biological enzyme: 15 to 30 parts;
   plant-based nonionic surfactant: 10 to 20 parts;
   antibacterial agent: 1 to 5 parts;
   stabilizer: 1 to 5 parts; and alcohol solvent: 10 to 20 parts;

wherein, the above components are measured by mass.

2. The biochemical viscosity reducer for heavy oil according to claim 1, wherein, the compound biological enzyme refers to four or more of esterase, lipase, protease, amylase, cellulase, amidase, oxidoreductase, fungal laccase, and peroxidase.

3. The biochemical viscosity reducer for heavy oil according to claim 1, wherein, the plant-based nonionic surfactant is tea saponin.

4. The biochemical viscosity reducer for heavy oil according to claim 1, wherein, the stabilizer comprises disodium ethylenediaminetetraacetic acid (EDTA) and/or sodium citrate.

5. The biochemical viscosity reducer for heavy oil according to claim 1, wherein, the antibacterial agent comprises tetrakis(hydroxymethyl)phosphonium sulfate (THPS) and/or potassium benzoate.

6. The biochemical viscosity reducer for heavy oil according to claim 1, wherein, the alcohol solvent comprises one or more of ethylene glycol (EG), propylene glycol (PG), and butylene glycol.

7. A preparation method of a biochemical viscosity reducer for heavy oil, comprising the following steps:

step 1: adding 30 to 60 parts of a *Brevibacillus borstelensis*-fermented mixed lipopeptide solution, 15 to 30 parts of a compound biological enzyme, 10 to 20 parts of a plant-based nonionic surfactant, and 1 to 5 parts of a stabilizer to a reactor, and stirring a resulting mixture at a controlled temperature of 50° C. to 60° C. for 50 min to 80 min; and step 2: adding 1 to 5 parts of an antibacterial agent and an alcohol solvent to the reactor, and stirring a resulting mixture for 60 min to 120 min, cooling to room temperature, and standing for 2 h to obtain a finished product of the viscosity reducer.

8. The preparation method of a biochemical viscosity reducer for heavy oil according to claim 7, wherein, the plant-based nonionic surfactant is tea saponin; the antibacterial agent comprises THPS and potassium benzoate; and the stabilizer comprises disodium EDTA and sodium citrate.

* * * * *